US009758500B2

(12) United States Patent
Weingarten et al.

(10) Patent No.: US 9,758,500 B2
(45) Date of Patent: *Sep. 12, 2017

(54) PROCESS FOR THE PREPARATION OF (3E, 7E)-HOMOFARNESOL

(71) Applicant: BASF SE, Ludwigshafen (DE)

(72) Inventors: Melanie Weingarten, Ludwigshafen (DE); Hansgeorg Ernst, Schweighofen (DE); Wolfgang Siegel, Limburgerhof (DE); Ekkehard Winterfeldt, Isernhagen (DE); Reinhard W. Hoffmann, Marburg (DE)

(73) Assignee: BASF SE, Ludwigshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/291,129

(22) Filed: Oct. 12, 2016

(65) Prior Publication Data

US 2017/0029396 A1 Feb. 2, 2017

Related U.S. Application Data

(63) Continuation of application No. 14/804,747, filed on Jul. 21, 2015, now Pat. No. 9,493,385, which is a continuation of application No. 13/863,860, filed on Apr. 16, 2013, now abandoned.

(60) Provisional application No. 61/642,432, filed on Apr. 16, 2012.

(51) Int. Cl.
C07D 307/92 (2006.01)
C07C 29/58 (2006.01)
C07C 17/08 (2006.01)
C07C 29/38 (2006.01)
C07C 13/04 (2006.01)

(52) U.S. Cl.
CPC ............ C07D 307/92 (2013.01); C07C 13/04 (2013.01); C07C 17/08 (2013.01); C07C 29/38 (2013.01); C07C 29/58 (2013.01); C07C 2101/02 (2013.01)

(58) Field of Classification Search
CPC ....... C07C 29/38; C07C 29/58; C07C 307/92; C07C 13/04; C07C 17/08; C07C 2101/02; C07D 307/92
USPC ........................................................ 549/458
See application file for complete search history.

(56) References Cited

U.S. PATENT DOCUMENTS

| 4,098,827 | A | 7/1978 | Rosenberger |
| 4,585,885 | A | 4/1986 | Bernhard et al. |
| 5,294,602 | A | 3/1994 | Brunke et al. |
| 5,714,642 | A | 2/1998 | Didion et al. |
| 6,596,520 | B1 | 7/2003 | Friedrich et al. |
| 7,057,030 | B2 | 6/2006 | Bramucci et al. |
| 9,493,385 | B2 * | 11/2016 | Weingarten ............ C07C 29/38 |
| 2007/0128704 | A1 | 6/2007 | Sturmer |
| 2008/0155302 | A1 | 6/2008 | Mue et al. |
| 2008/0177100 | A1 | 7/2008 | Eberhardt et al. |
| 2008/0206824 | A1 | 8/2008 | Sturmer et al. |
| 2010/0143991 | A1 | 6/2010 | Breuer et al. |
| 2010/0291640 | A1 | 11/2010 | Stuermer et al. |
| 2010/0291641 | A1 | 11/2010 | Dauwel et al. |
| 2011/0145970 | A1 | 6/2011 | Subkowski et al. |
| 2011/0250655 | A1 | 10/2011 | Schneider et al. |
| 2011/0275855 | A1 | 11/2011 | Ditrich et al. |
| 2012/0070867 | A1 | 3/2012 | Maurer et al. |
| 2012/0114726 | A1 | 5/2012 | Leininger et al. |
| 2012/0114727 | A1 | 5/2012 | Leininger et al. |
| 2012/0123155 | A1 | 5/2012 | Hauer et al. |
| 2012/0135477 | A1 | 5/2012 | Breuer et al. |
| 2012/0237991 | A1 | 9/2012 | Breuer et al. |
| 2012/0263659 | A1 | 10/2012 | Subkowski et al. |

FOREIGN PATENT DOCUMENTS

| DE | 3139358 A1 | 4/1983 |
| DE | 10019377 A1 | 10/2001 |
| DE | 102006056526 A1 | 6/2008 |
| EP | 101597 A2 | 2/1984 |
| EP | 490326 A2 | 6/1992 |
| EP | 0491127 A1 | 6/1992 |
| EP | 1069183 A2 | 1/2001 |
| EP | 1149849 A1 | 10/2001 |
| SU | 776048 A | 9/1983 |
| WO | WO9100920 A2 | 1/1991 |
| WO | WO-2005/073215 A1 | 8/2005 |
| WO | WO-2006106141 A1 | 10/2006 |
| WO | WO-2007072529 A2 | 6/2007 |
| WO | WO-2008154243 A1 | 12/2008 |
| WO | WO-2008155302 A1 | 12/2008 |
| WO | WO-2010026094 A1 | 3/2010 |
| WO | WO-2010079068 A1 | 7/2010 |
| WO | WO-2010081865 A1 | 7/2010 |

(Continued)

OTHER PUBLICATIONS

Ronvaux, Synthesis of Oxidio-2,3-polyenes and the study of their reactivity via the 2,3-epoxysqualene sterolcyclase liver and *Saccharomyces cerevisiae*, Dissertation, Sel. Org. React. Database (SORD) 1999,(Oct. 4, 2012), abstact (p. 2).*
Barrero, A., et al., "Synthesis of (=)-Ambrox from (E)-Nerolidol and β-Ionone via Allylic Alcohol [2,3] Sigmatropic Rearrangement", J. Org. Che., vol. 61, (1996), pp. 2215-2218.
Bestmann, H., et al., "Darstellung Und Reaktionen Des Triphenylphosphin-Cyclo-Propylidens", Tetrahedron Letters, No. 30, (1996), pp. 3591-3593.
Bestmann, V., et al., "Bildung von Yliden bei der thermischen Zersetzung von Triphenyl-x-alkoxycarbonylalkyl-phosphoniumsalzen", Angewandte Chemie, vol. 77, (1965), pp. 1101-1102.
Bradshaw et al., "Lactobacillus Kefir Alcohol Dehydrogenase: A Useful Catalyst for Synthesis", J. Org. Chem., vol. 57, No. 5, pp. 1532-1536 (1992).

(Continued)

Primary Examiner — T. Victor Oh
(74) Attorney, Agent, or Firm — Drinker Biddle & Reath LLP

(57) ABSTRACT

The present invention relates to new types of processes for the improved preparation of homofarnesol, in particular of (3E,7E)-homofarnesol and homofarnesol preparations with an increased content of (3E,7E)-homofarnesol (also referred to as all E-homofarnesol).

15 Claims, No Drawings

(56) References Cited

FOREIGN PATENT DOCUMENTS

| WO | WO-2010130608 A2 | 11/2010 |
|---|---|---|
| WO | WO-2010130616 A1 | 11/2010 |
| WO | WO-2010139651 A2 | 12/2010 |
| WO | WO-2010139719 A2 | 12/2010 |
| WO | WO-2011003845 A2 | 1/2011 |
| WO | WO-2011003861 A2 | 1/2011 |
| WO | WO-2011009849 A2 | 1/2011 |
| WO | WO-2011012632 A2 | 2/2011 |
| WO | WO-2011032990 A1 | 3/2011 |
| WO | WO-2011036233 A1 | 3/2011 |
| WO | WO-2011061330 A2 | 5/2011 |
| WO | WO-2011064259 A1 | 6/2011 |

OTHER PUBLICATIONS

Brandi, A., et al., "Synthesis of Methylene- and Alkylidenecyclopropane Derivatives", Chem. Rev., vol. 98, (1998), pp. 589-635.
Carosati, et al., "Discovery of Novel and Cardioselective Diltiazem-like Calcium Channel Blockers via Virtual Screening", J. Med. Chem., (2008), vol. 51, No. 18, pp. 5552-5565.
Derwent DE102006056526 (Oct. 2, 2012).
Dodd, D., et al., "Synthesis of Inhibitors of 2,3 Oxidosqualene-Ianosterol Cyclase: Cojugate Addition of Organocuprates to N-(Carbobenzyloxy-3-carbomethoxy-5,6-dihydro-4-pyridone", J. Org. Chem., vol. 57, (1992), pp. 2794-2803.
Ernst, "Recent Advances in Industrial Carotenoid Synthesis", Pure Appl. Chem., vol. 74, No. 11 (2002) pp. 2213-2226.
Fahrenholtz, et al., "Octahydrophenanthrene Analogs of Tetrabenazine", J. Med. Chem., (1966), vol. 9, No. 3, pp. 304-310.
Fraâter, G., et al., "Fragance Chemistry", Tetrahedron, vol. 54, (1998), pp. 7633-7703.
Frenken et al., "Cloning of the Pseudomonas glumae lipase gene and determination of the active site residues", Appl. Environ. Microbiol., 58(12) (1992) pp. 3787-3791.
Fliszár, S., et al., "172. Etude du méchanisme de la réaction des dérivés phosphométhyléniques et des phosphobétaines avec le benzaldéhyde", Helvetica Chimica Acta, vol. 46, (1963), pp. 1580-1588.
Giersig, M., et al., "Fünffache Cyclobutylmethyl-Cyclopentyl-Umlagerung and einem Pentaspiro [3.03.03.03.03.1]henicosanol—Eine Schlüsselsequencz zur Synthese des [6.5] Coronans", Chem. Ber., vol. 121, (1988), pp. 525-531.
"Carotenoids", vol. 2: Synthesis (1996) pp. 281-284.
Guiseppin et al., (WO9100920-A. published Jan. 24, 1991).
Groger et al., "Preparative asymmetrric reduction of ketones in a biphasic medium with an (S)-alcohol dehydrogenase under in situ-cofactor-recycling with a formate dehydrogenase", Tetrahedron, vol. 60, pp. 633-640 (2004).
Hummel, "Large-scale applications of NAD(P)-dependent oxidoreductases: recent developments", Trends Biotechnology, vol. 17, pp. 487-492. (1999).
Ishihara, K., et al., "Enantio- and Diastereoselective Stepwise Cyclization of Polyprenoids Induced by Chiral and Achiral LBAs. A New Entry to (−)-Ambrox, (+)-Podocarpa-8,11,13-triene Diterpenoids, and (−)-Tetracyclic Polyprenoid of Sedimentary Origin", J. Am. Chem. Soc., vol. 124, (2002), pp. 3647-3655.
Kato et al., "Novel Heme-Containing Lyase, Phenylacetaldoxime Dehydratase from Bacillus sp. Strain OxB-1: Purification, Characterization, Molecular Cloning of the Gene", Biochemistry 39 (2000) pp. 800-809.
Kocieński, P., et al., "A Highly Stereoselective and Iterative Approach to Isoprenoid Chains: Synthesis of Homogeraniol, Homofarnesol, and Homogeranylgeraniol", J. Org. Chem., vol. 54, (1989), pp. 1215-1217.
Lalonde et al., "Enzyme Catalysis in Organic Synthesis", Comprehensive Handbook vol. 1, pp. 163-184.
Kahlow et al., A model of the pressure dependence of the enantioselectivity of Candida rugosa lipase towards (±)-menthol Protein Science (2001), vol. 10, pp. 1942-1952.

Leffingwell, J., et al., "Chiral chemistry in flavours & fragances", Specialty Chemical Magazine, vol. 30, (2011), pp. 30-33.
Maercker, A., et al., "Polylithiumorganic Compounds—19.1 Regioselective Carbon-Carbon o-Bond Scission followed by a 1,6-Proton shift upon the Reductive Metalation of Benzylidenecyclopropane Derivatives with Lithium Metal", Tetrahedron, vol. 50, No. 8, (1994), pp. 2439-2458.
Matsuda et al., "Tetrahedron Asymmetry", vol. 20, Issue 5, pp. 513-557 (2009).
Menéndez, et al., "The Reactivity of 2-Iminobenzo[α]Quinolizidines Towards 2-Mercaptoacetic Acid", Heterocycles, (1990), vol. 31, No. 11, pp. 2065-2071.
Nakamura et al., "Reduction Reactions", Enzyme Catalysis in Organic Synthesis, vol. 3, No. 15, pp. 991-1032 (Nov. 16, 2011).
Nishihara et al., "Chaperone Coexpression Plasmids: Differential and Synergistic Roles of DnaK-DnaJ-GrpE and GroEl-GroES in Assisting Folding of an Allergen of Japanese Cedar Pollen, Cryj2, in *Escherichia coli*", Appl. Envornm. Microbiol. 64(5) (1998) pp. 1694-1699.
Ohloff, G., et al., "212. Significance of the Geminal Dimethyl Group in the Odor Principle of Ambrox", Helvetica Chimica Acta, vol. 68, (1985), pp. 2022-2029.
Popp, et al., "Synthesis of Potential Antineoplastic Agents XXVI: 1,3,4,6,7,11b-Hexahydro-9,10-dimethoxy-2H-benzo[α]2-quinolizinone Derivatives", J. Pharm Sci., (1978), vol. 67, No. 6, pp. 871-873.
Rosenberger et al., "Canthaxanthin. A New Total Synthesis", J. Org. Chem., vol. 47, (1982) pp. 2130-2134.
Rubiralta, et al., "New Synthesis of Benzo [α] Quinolizidin-2-ones via Protected 2-aryl-4-piperidones", Tetrahedron, (1987), vol. 43, No. 13, pp. 3021-3030.
Sanchez et al., "Continuous enantioselective esterification of trans-2-phenyl-1-cyclohexanol using a Candida rugosa lipase in a packed bed bioreactor", Journal of Biotechnology vol. 84 (2000) pp. 1-12.
Schäfer, "Unwiderstehliche Dufnote—Ambrox", Chem. Unserer Zeit, vol. 45, (2011), pp. 374-388.
Schweizer, E., et al., "Reactions of Phosphorus Compounds. XIII. Preparations and Reactions of Cyclopropyltriphenylphosphonium Bromide", The Journal of Organic Chemistry, (1968), vol. 33, pp. 336-339.
Schweizer, E., et al., "Reactions of Phosphorous Compunds. Preparation of Cyclopropylidene Compounds from Cyclopropyltriphenylphosphonium Bromide", J. Chem. Soc., Chem. Comm., (1966), pp. 666-667.
Sisido, K., et al., "Diphenymethlenecyclopropane", Tetrahedron Letters, No. 28, (1966), pp. 3267-3270.
Snowden, R., et al., "Cetalox and Analogues: Synthesis via Acid-Mediated Polyene Cyclizations", Chemistry & Biodervisty, vol. 5, (2008), pp. 958-969.
Snowden, R., et al., "Internal Nucleophilic Termination in Biomimetric Acid Mediated Polyene Cyclizations: Sterochemical and Mechanistic Implications. Synthesis of (+) Ambrox and Its Diastereoisomers", J. Org. Chem., vol. 57, (1992), pp. 955-960.
Szántay, et al., "Azaberbene Derivatives as α2A-Adrenoceptor Antagonists", Arch. Pharm., (2002), vol. 335, No. 1, pp. 22-26.
Utimoto, K., et al., "Preparation and Reaction of Cyclopropyltripenylphosphonium Salt", Tetrahedron, vol. 29, (1973), pp. 1169-1171.
Vlad, P., et al., "Superacid Cyclization of Homo- and Bishomoisoprenoid Acids", (1991), pp. 246-249.
Xie et al., High Yield Synthesis of Nitriles by a New Enzyme, Phenylacetaldoxime Dehydratase, from Bacillus sp. Strain OxB-1, Biosci. Biotechnol. Biochem. 65(12) (2001) pp. 2666-2672.
Yang et al., "Enhancing the stereoselectivity and activity of Candida species lipase in organic solvent by noncovalent enzyme modification", Ann NY Acad Sci., 799; (Oct. 12, 1996) pp. 358-363.
Yu et al., "Preparation and Characterization of Tetrabenazine Enantiomers against Vesicular Monoamine Transporter 2", ACS Medicinal Chemistry Letters, (2010), vol. 1, No. 3, pp. 105-109.
Zahalka, H., et al., "One-Pot Conversion of Primary Alkyl Chlorides and Dichlorides into Alcohols, Diols, and Ethers via Formic Ester Intermediates under Phase-Transfer Conditions", Synthesis, (1986), pp. 763-765.

(56) References Cited

OTHER PUBLICATIONS

Translation of the International Preliminary Report on Patentability for PCT/EP2012/068538 dated Mar. 25, 2014.
International Search Report for PCT/EP2011/070607 dated Feb. 17, 2012.
Database Chemabs, Itoh, N., et al., Database Accession No. 1960-56497, 1959.
Database Chemabs, King et al., Database Accession No. 1959-99863, dated 1958.
Database Chemabs, Itoh, N., et al., Database Accession No. 1959-99862, dated 1959.

* cited by examiner

PROCESS FOR THE PREPARATION OF (3E, 7E)-HOMOFARNESOL

CROSS-REFERENCE TO RELATED APPLICATIONS

This application is a continuation application of U.S. patent application Ser. No. 14/804,747 filed on Jul. 21, 2015, which in turn is a continuation application of U.S. application Ser. No. 13/863,860 filed on Apr. 16, 2013, which in turn claims priority to U.S. Provisional Application 61/624,432 filed Apr. 16, 2012, under 35 USC 119(e), the applications of which are each incorporated herein by reference in their entirety.

The present invention relates to new types of processes for the improved preparation of homofarnesol, in particular of (3E,7E)-homofarnesol and homofarnesol preparations with an increased content of (3E,7E)-homofarnesol (also referred to as all E-homofarnesol).

BACKGROUND OF THE INVENTION

Ambrox® is the trade name of the enantiomerically pure compound (−)-ambrox (3aR,5aS,9aS,9bR)-3a,6,6,9a-tetramethyldodecahydronaphtho[2,1-b]furan), a sought-after fragrance. Naturally occurring (−)-ambrox is the olfactory most important ingredient of ambergris, a digestion product of sperm whales.

The different diastereomers of (−)-ambrox have a similar scent, but sometimes differ in their odor thresholds (G. Ohloff, W. Giersch, W. Pickenhagen, A. Furrer, B. Frei, Helv. Chim. Acta 68 (1985) 2022. G. Frater, J. A. Bajgrowicz, P. Kraft, Tetrahedron 54 (1998) 7633). The odor threshold of 3a-epi-(−)-ambrox is higher than that of (−)-ambrox by a factor of 100. By contrast, 9b-epi-(−)-mbrox has half as high an odor threshold as (−)-ambrox for virtually the same odor quality. (+)-Ambrox is eight times weaker than the natural enantiomer. The racemate has an odor threshold of 0.5 ppb and barely differs from that of (−)-Ambrox® in its tonalities. (B. Schäfer Chemie in unserer Zeit 2011, 45, 374).

Homofarnesol is an important intermediate of synthesis processes for preparing Ambrox® (R. L. Snowden, Chemistry & Biodiversity 2008, 5, 958. J. and D. Leffingwell Specialty Chemical Magazine 2011, 30).

In particular, the cyclization of all E-homofarnesol of the formula Ia

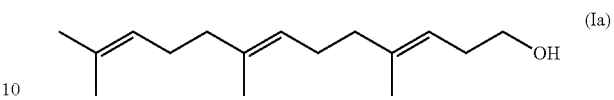

produces diastereomerically pure or enantiomerically pure ambrox (Super acids: P. F. Vlad et al. Khimiya Geterotsiklicheskikh Soedinenii, Engl. Transl. 1991, 746; R. L. Snowden, Chemistry & Biodiversity 2008, 5, 958. Lewis acid-Brönsted acid: K. Ishihara at al. J. Am. Chem. Soc. 2002, 124, 3647. Mechanistic investigations: R. L. Snowden et al. J. Org. Chem. 1992, 57, 955.).

The literature describes various processes for preparing all E-homofarnesol:

(1) stereoisomerically pure (3E,7E)-homofarnesol can be prepared from (E,E)-farnesol via (E,E)-farnesal, C1 extension according to Wittig with methylenetriphenyl-phosphorane and subsequent terminal hydroboration of the conjugated diene in accordance with a synthesis described in the literature (D. S. Dodd et al. J. Org. Chem, 1992, 57, 2794).

However, this synthesis is not a technically-economically sensible route to (E,E)-homofarnesol. A technical process for preparing isomerically pure farnesol is not given.

(2) An alternative known in the literature for the synthesis of (3E,7E)-homofarnesol consists in the following procedure (A. F. Barrero et al. J. Org. Chem. 1996, 61, 2215.): a) distillative separation of (E/Z)-nerolidol, b) reaction of (E)-nerolidol with dimethylformamide dimethylacetal (DMFDMA) in a Büchi rearrangement to give the corresponding (3E/Z, 7E)-$C_{16}$-amides, c) flash-chromatographic separation of the stereoisomeric amides and d) reduction of the (3E,7E)-amide to the corresponding (3E,7E)-homofarnesol with lithium triethylborohydride. Disadvantages of this route are the moderate yields and the required flash chromatography for separating the stereoisomers.

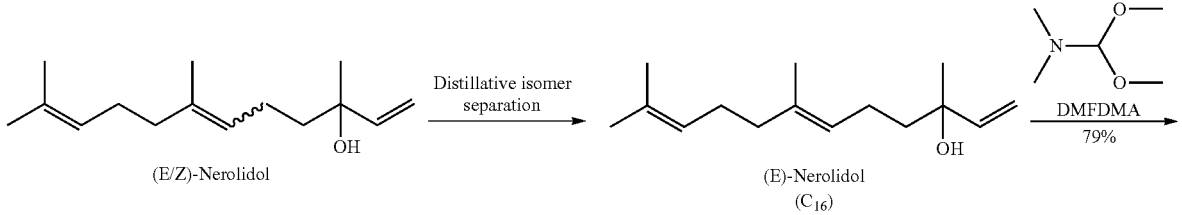

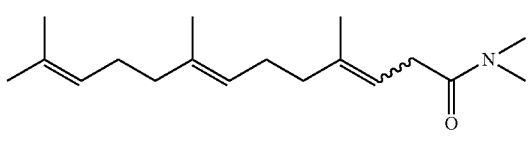

(3E/Z,7E)-homofarnesylic acid amide
(3E):(3Z) ca. 2.2:1

Column chromatography

-continued

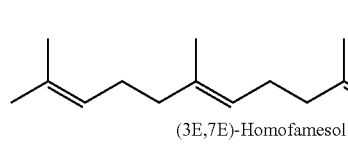
(3E,7E)-Homofarnesol

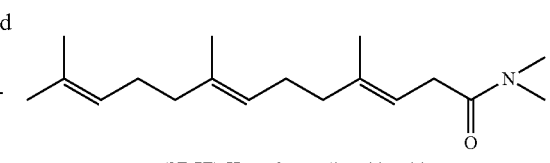
(3E,7E)-Homofarnesylic acid amide (3) A patent application from Henkel (WO 92/06063, Henkel Research Corporation) describes the carbonylation of (E)-nerolidol with the addition of catalytic amounts of the relatively expensive reagent palladium (II) chloride. Furthermore, the reaction takes place disadvantageously for the implementation at high CO pressures of ca. 70 bar.

lation of 5-lithio-2,3-dihydrofuran with a homoallylic iodide followed by Ni(O)-catalyzed coupling with methylmagnesium bromide. The resulting homogeraniol can be converted to the corresponding iodide and the cycle is repeated. The synthesis is E-selective and produces the homofarnesol over 5 stages in an overall yield of ca. 70%.

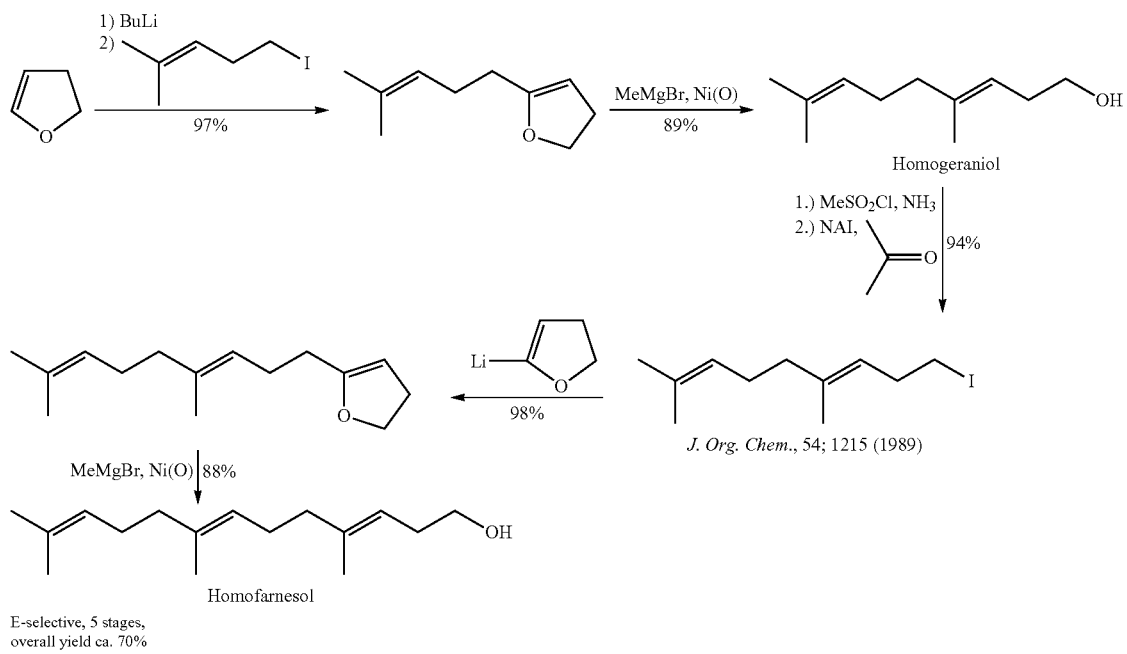

J. Org. Chem., 54; 1215 (1989)

Homofarnesol
E-selective, 5 stages,
overall yield ca. 70%

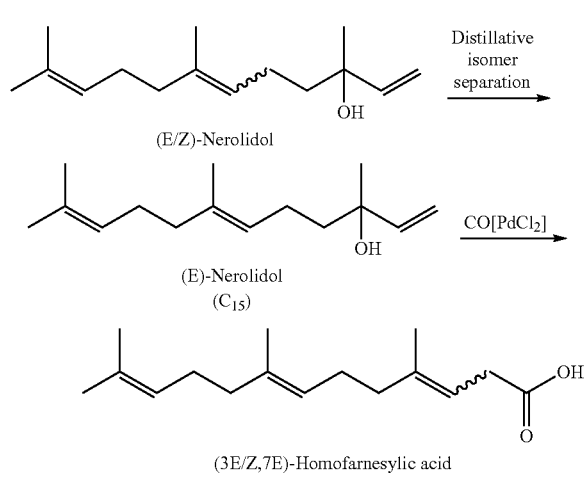

(4) A further literature source (P. Kocienski et al. *J. Org. Chem.* 1989, 54, 1215.) describes the synthesis of homofarnesol from dihydrofuran. Each cycle requires the alky- The first three processes described above never arrive directly at the oxidation state of homofarnesol. Furthermore, expensive hydride reagents are required for reducing the homofarnesylic acid. Process (4) is economically unattractive on account of the reagents required.

The objective of the invention is therefore the provision of an improved process for the preparation of homofarnesol, in particular (3E,7E)-homofarnesol, and structurally analogous compounds.

SUMMARY OF THE INVENTION

This object was achieved in general by the process according to the invention as per claim 1 and in particular by a specific embodiment of this process for the preparation of (3E,7E)-homofarnesol.

The synthesis strategy is essentially based on the coupling of a $C_{13}$- and $C_3$-building block in a Wittig reaction. The $C_3$ building block is the cyclopropylphosphonium salt known in the literature (A. Brandi et al. *Chem. Rev.* 1998, 589 and literature cited therein). The $C_{13}$ building block geranyl acetone is available industrially and cost-effectively as intermediate from the citral value-addition chain. The desired (E)-isomer is obtainable by distillation. This coupling strategy can be transferred to shorter- or longer-chain homologs of the $C_{13}$ building block geranyl acetone.

DETAILED DESCRIPTION OF THE INVENTION a) General Definitions

Unless statements are made to the contrary, the following general meanings are applicable:

"Ambrox" comprises in particular (−)-ambrox of the formula

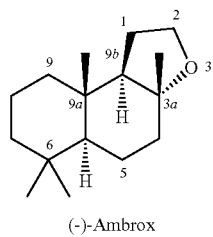

(−)-Ambrox in stereoisomerically pure form or optionally in a mixture with at least one of the following diastereomers:

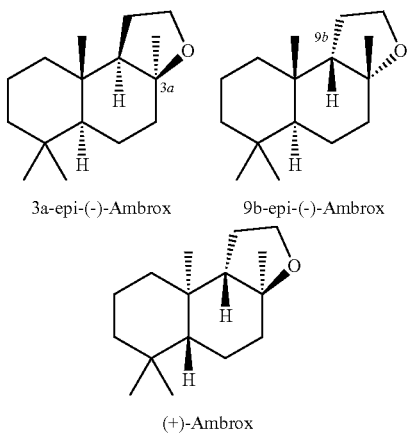

3a-epi-(−)-Ambrox    9b-epi-(−)-Ambrox (+)-Ambrox

"Enantiomerically pure" means that, besides the specifically named enantiomer, no other enantiomeric form of a chemical compound having at least one center of a symmetry can be detected analytically.

"Hydrocarbyl" is to be interpreted in the wide sense and comprises straight-chain or mono- or polybranched hydrocarbon radicals having 1 to 50 carbon atoms which can optionally additionally comprise heteroatoms, such as e.g. O, N, NH, S, in their chain. In particular, hydrocarbyl stands for straight-chain, and especially mono- or polybranched hydrocarbon radicals of the above chain length but without heteroatom. Hydrocarbyl comprises, for example, the alkyl or alkenyl radicals defined below and substituted analogs thereof, in particular straight-chain or branched $C_1$-$C_{20}$, $C_1$-$C_{10}$- or $C_1$-$C_6$-alkyl radicals, or straight-chain or branched, monounsaturated or polyunsaturated, like 1-, 2-, 3-, 4- or 5-fold unsaturated alkenyl radicals with conjugated or in particular non-conjugated double bonds.

"Alkyl" stands in particular for saturated, straight-chain or branched hydrocarbon radicals having 1 to 4, 1 to 6, 1 to 8, 1 to 10, 1 to 14 or 1 to 20, carbon atoms, such as e.g. methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methyl pentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl; and also n-heptyl, n-octyl, n-nonyl and n-decyl, n-dodecyl, n-tetradecyl, n-hexadecyl, and also the mono- or polybranched analogs thereof.

"Alkoxy" stands for the °alkyl analogs of the above alkyl radicals, such as e.g. methoxy, ethoxy, n-propoxy, 1-methylethoxy, butoxy, 1-methylpropoxy, 2-methylpropoxy or 1,1-dimethylethoxy; and also e.g. pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy or 1-ethyl-2-methylpropoxy.

"Alkenyl" stands in particular for the unsaturated, straight-chain or branched analogs of the above alkyl radicals and have in particular 2 to 4, 2 to 6, 2 to 8, 2 to 10, 2 to 14 or 2 to 20, carbon atoms. In particular, these can be monounsaturated or polyunsaturated, such as e.g. diunsaturated, triunsaturated, tetraunsaturated or pentaunsaturated. The double bonds here are non-cumulated double bonds. In particular, the double bonds are conjugated or in particular non-conjugated. For example, a suitable alkenyl radical optionally comprises repetitive isoprene-like structural elements

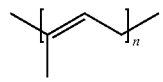

where n can be a whole-numbered value from 1 to 8, such as e.g. 1, 2, 3 or 4.

"Acyl" (as such or as part of "Oacyl" radicals) stands in particular for radicals derived from straight-chain or branched, optionally mono- or polyunsaturated, optionally substituted $C_1$-$C_{24}$-, such as e.g. $C_1$-$C_6$- or $C_1$-$C_4$-monocarboxylic acids. For example, acyl radicals which can be used are derived from the following carboxylic acids: saturated acids, such as formic acid, acetic acid, propionic acid and n- and i-butyric acid, n- and isovaleric acid, caproic acid, oenanthic acid, caprylic acid, pelargonic acid, capric acid, undecanoic acid, lauric acid, tridecanoic acid, myristic acid, pentadecanoic acid, palmitic acid, margaric acid, stearic acid, nonadecanoic acid, arachic acid, behenic acid, lignoceric acid, cerotic acid and melissic acid; monounsaturated acids, such as acrylic acid, crotonic acid, palmitoleic acid, oleic acid and erucic acid; and diunsaturated acids, such as sorbic acid and linolic acid. If double bonds are present in the fatty acids, then these can be present either in the cis form or in the trans form.

"Aryl" stands in particular for mono- or polynuclear, preferably mono- or dinuclear, in particular mononuclear, optionally substituted aromatic radicals having 6 to 20, such as e.g. 6 to 10, ring carbon atoms, such as e.g. phenyl, biphenyl, naphthyl, such as 1- or 2-naphthyl, tetrahydronaphthyl, fluorenyl, indenyl and phenanthrenyl. These aryl radicals can optionally carry 1, 2, 3, 4, 5 or 6 identical or different substituents, for example selected from halogen, alkyl, in particular having 1 to 4 carbon atoms, alkenyl, in particular having 2 to 4 carbon atoms, OH, alkoxy, in particular having 1 to 4 carbon atoms, acyl, in particular having 1 to 4 carbon atoms, $NH_2$ or $NO_2$.

"Halogen" stands for F, Cl, Br or I.

b) Specific Embodiments

The present invention relates in particular to the following embodiments:

1. Process for the preparation of compounds of the general formula I

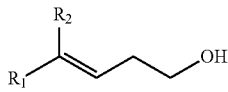

in which
$R_1$ is a straight-chain or branched, optionally monounsaturated or poly- (such as e.g. mono- or di-) unsaturated hydrocarbyl radical, e.g. $C_1$-$C_{20}$, $C_1$-$C_{11}$ or $C_1$-$C_6$ hydrocarbyl, like in particular a straight-chain or branched $C_1$-$C_{20}$, $C_1$-$C_{11}$ or $C_1$-$C_6$ alkyl radical or a straight-chain or branched $C_2$-$C_{20}$-, $C_2$-$C_{10}$- or $C_2$-$C_6$-alkenyl radical with one or more conjugated or non-conjugated double bonds, or e.g. a radical of the isoprene type of the formula

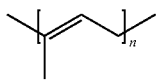

in which n is 1, 2, 3, 4 or 5;
and $R_2$ is H or $C_1$-$C_6$-alkyl, in particular methyl or ethyl, where
a) a carbonyl compound of the formula II

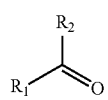

in which $R_1$ and $R_2$ have the meanings given above, is reacted by means of Wittig olefination to give a cyclopropane of the general formula (III)

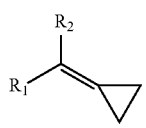

in which $R_1$ and $R_2$ have the meanings given above,
b) the cyclopropane of the formula III is reacted, with ring opening, to give a compound of the formula IV

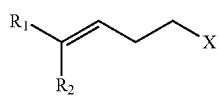

in which $R_1$ and $R_2$ have the meanings given above, and X is halogen, such as e.g. Cl or Br, or O—R", in which R' is H, acyl, such as $C_1$-$C_4$-acyl, in particular acetyl, Tf-acetyl or $SO_2$—R", in which R" is alkyl, in particular $C_1$-$C_4$-alkyl or optionally substituted aryl, in particular optionally substituted phenyl;
and
c) the compound of the general formula IV is converted to the compound of the general formula I.

2. Process according to embodiment 1, where a cyclopropylphosphonium salt is used for the Wittig olefination according to stage a).

3. Process according to embodiment 2, in which the cyclopropylphosphonium salt is a triphenylphosphonium compound of the formula V

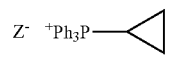

in which $Z^-$ is the anion of a strong acid, such as in particular a halide, such as e.g. fluoride, chloride or bromide, preferably bromide.

4. Process according to embodiment 3, where the compound of the formula V is prepared by a) reacting bromobutyrolactone with triphenylphosphine and then thermally decarboxylating the reaction product, or b) reacting 1,3-dibromopropane with triphenylphosphine, in particular in the presence of a base, such as in particular a base without nucleophilic properties (such as e.g. PhLi, NaH, K tert-butylate) and then cyclizing the reaction product.

5. Process according to one of the preceding embodiments, in which the ring opening of stage b) takes place in the presence of a Lewis acid (such as e.g. $AlCl_3$, $BF_3$, $SiCl_4$, $PF_5$, $Sn(OTf)_2$, $Cu(OTf)_2$) or Brönstedt acid/protonic acid (such as, e.g. formic acid, acetic acid, propionic acid, sulfuric acid, pivalic acid, isobutyric acid, alkyl- and arylsulfonic acids, e.g. methanesulfonic acid or para-toluenesulfonic acid) and of a nucleophile (such as e.g. $OH^-$, formate, acetate, propionate, pivalate, isobutyrate, alkyl- and arylsulfonate, e.g. methanesulfonate or para-toluenesulfonate, chloride, bromide), where Tf is trifluoromethanesulfonyl.

6. Process according to embodiment 5, where the ring opening takes place essentially stereoselectively, in particular E-selectively (with respect to $R_1$).

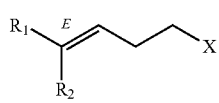

E-selectivity is present here particularly when, after ring opening, the E form is formed in quantitative (molar) excess (i.e. E:Z>1, such as e.g. >1.01, such as e.g. >1.5 or >2, such as e.g. in the range from 1.5 to 100, 2 to 50 or 2.2 to 10; or E is formed quantitatively, i.e. Z form cannot be detected analytically, 7. Process according to one of the preceding embodiments, where, in stage c), the compound of the general formula IV is converted to a compound of the general formula I by, when X is Oacyl, such as e.g. Oacetyl, carrying out an ester cleavage, or when X is halogen, such as e.g. Cl or Br, converting the halide into an ester, as e.g. with a salt of formic acid (e.g. sodium formate) to the corresponding formic acid ester and then cleaving this ester.

8. Process according to one of the preceding embodiments, in which a product comprising a (3E,7E)-homofarnesol of the formula Ia

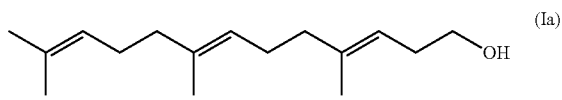 [SMILES: CC(C)=CCC/C(C)=C/CC/C(C)=C/CCO]
(Ia)

is obtained.

9. Process according to embodiment 8, where, in stage a), E-geranyl acetone of the formula IIa

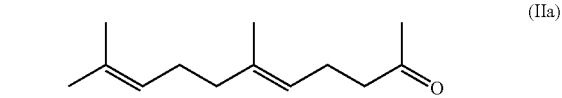
(IIa)

is reacted with cyclopropylphosphonium halide such that the cyclopropane of the formula IIIa

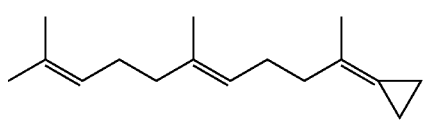
(IIIa)

is obtained.

10. Compounds of the formula III, in particular of the formula IIIa.

11. Process for the preparation of enantiomerically pure ambrox or of a stereoisomer mixture of ambrox, where (3E,7E)-homofarnesol is prepared according to a process as per one of the proceeding embodiments 1 to 9, and the homofarnesol formed in this way is reacted chemically or enzymatically in a manner known per se to give enantiomerically pure or racemic ambrox or any desired stereoisomer mixtures thereof.

c) Detailed Description of the Process According to the Invention

The principle of the process according to the invention is illustrated in more detail by reference to a preferred embodiment for the preparation of all E-homofarnesol, without being limited to this specific reaction. Specific configurations can therefore be transferred to other starting compounds used.

The $C_{16}$ building block (E)-$C_{16}$-cyclopropane can be obtained by Wittig olefination of (E)-geranyl acetone with the cyclopropyltriphenylphosphonium salt as follows:

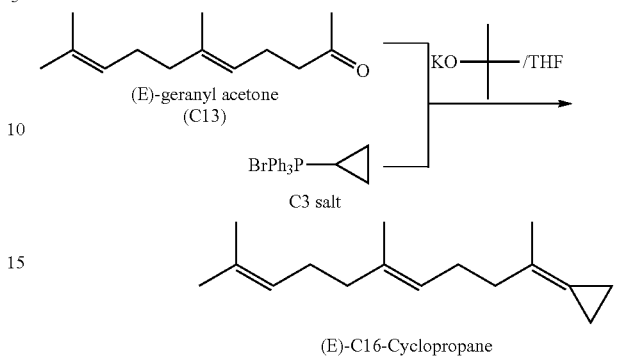

The $C_3$ salt can be prepared in accordance with procedures in the literature from α-bromobutyrolactone in two stages via a $C_4$ salt as intermediate (S. Fliszár et al. *Helv. Chim. Acta* 1963, 46, 1580. H. J. Bestmann et al. *Tetrahedron Lett.* 1966, 3591. E. E. Schweizer et al. *J. Chem. Soc., Chem. Comm.* 1966, 666. H. J. Bestmann et al. *Angewandte Chemie* 1965, 77, 1011.):

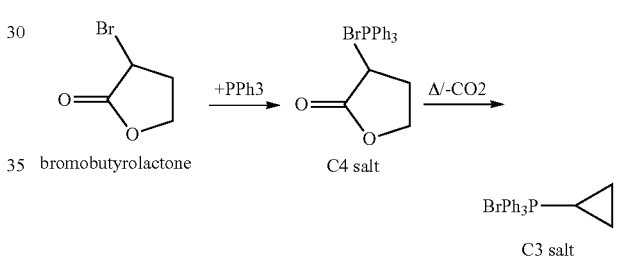

An alternative to the $C_3$ salt synthesis starting from 1,3-dibromopropane is likewise known in the literature (K. Sisido et al. *Tetrahedron Lett.* 1966, 3267. A. Maercker et al. *Tetrahedron* 1994, 50, 2439. K. Utimoto et al. *Tetrahedron* 1973, 29, 1169., E. E. Schweizer et al. *J. Org. Chem.* 1968, 33, 336.):

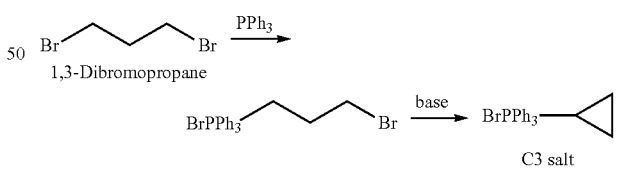

Classic Wittig olefinations with cyclopropyltriphenylphosphonium bromide have only been described little in the literature (A. Brandi et al. *Chem. Rev.* 1998, 589 and literature cited therein. M. Giersig et al. *Chem. Ber.* 1988, 525.). The yields for these Wittig reactions with various ketones (e.g. cyclohexanone, benzophenone) are between 43% and 80%. To avoid secondary reactions, bases without nucleophilic properties (PhLi, NaH, K tert-butylate) are used, as in the present case the relatively cost-effective base K tert-butylate or NaH. In general, in the Wittig reactions, the yields for trisubstituted olefins are generally low, and for tetrasubstituted olefins are even worse (H. G. Ernst, Carotenoids, Volume 2, Synthesis, P. 80f.).

Surprisingly, it has been established according to the invention that the Wittig olefination of cyclopropyltriphenylphosphonium bromide with an aliphatic ketone such as (E)-geranyl acetone using potassium tert-butylate to give (E)-$C_{16}$-cyclopropane proceeds in yields >90% (see example 1). The Wittig reaction can take place using 2 eq of NaH also starting from TPP-bromopropane salt and in situ cyclization to the cyclopropylphosphonium salt in a very good yield of >90% (see example 2).

(E)-$C_{16}$-cyclopropane, which is hitherto unknown in the literature, can be opened in the presence of an acid, e.g. a Lewis acid such as $AlCl_3$ or $BF_3*Et_2O$ and a nucleophile in a regioselective and stereoselective way to give homofarnesyl derivates.

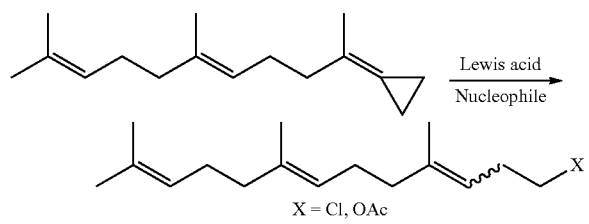

X = Cl, OAc

The ring opening of alkylidene cyclopropane derivatives has been described in the literature (H. Pellissier *Tetrahedron* 2010, 66, 8341 and literature cited therein), although, as happened in our case, no side chains with double bonds were observed (see examples 3 and 4).

Homofarnesyl chloride can then be converted to homofarnesol by means of classic acetate substitution and hydrolysis. Alternatively, homofarnesoyl can be synthesized in accordance with the literature (H. A. Zahalka at al. *Synthesis* 1986, 763.) starting from homofarnesyl chloride via the formate and subsequent hydrolysis (see example 5).

3E,7E- and 3Z/7E-homofarnesol and the corresponding 3Z-isomers can be separated by distillation such that pure 3E,7E-homofarnesol is obtained.

The homofarnesol obtained in this way can then be cyclized in a further step to give ambrox (see example 6).

This cyclization can take place here in a manner known per se or as described in the working examples below. Both enzymatic and chemical cyclizations are contemplated for this purpose.

Thus, for example, the enzymatic cyclization by means of squalene hopene cyclase is known from WO 2010/139719, to which reference is hereby expressly made.

Chemical cyclization reactions using a super acid (fluorosulfonic acid in 2-nitropropane) are known e.g. from P. F. Vlad et al. *Khimiya Geterotsiklicheskikh Soedinenii, Engl. Transl.* 1991, 746. Further processes comprise a cyclization comprising the enantioselective polyene cyclization of homofarnesyl triethylsilyl ether in the presence of O-(o-fluorobenzyl)binol and $SnCl_4$, as described by Yamamoto (H. Yamamoto et al. *J. Am. Chem. Soc.* 2002, 3647.)

EXPERIMENTAL SECTION

A) Material and Methods

HPLC Analysis:
Method 1)
Instrument Settings and Chromatographic Conditions:

Instrument: Agilent Series 1100
Column: Zorbax Eclipse XDB-C18 1.8 µm 50*4.6 mm combined with a Zorbax Extend C18 1.8 µm 50*4.6 mm from Agilent®
Eluent: –A: Water with 0.1% by volume $H_3PO_4$
–B: Acetonitrile with 0.1% by volume $H_3PO_4$

| Time in min | % B | Flow |
|---|---|---|
| 0.0 | 70 | 1 |
| 10.0 | 80 | 1 |
| 13.0 | 100 | 1 |
| 17.0 | 100 | 1 |
| 17.1 | 70 | 1 |

Detector: UV detector λ=197 nm, BW=4 nm
Flow rate: 1 ml/min
Injection: 1 µL
Temperature: 50° C.
Run time: 20 min
Pressure: ca. 160 bar
Method 2)
Instrument Settings and Chromatographic Conditions
Instrument: Agilent Series 1100
Column: Chiralpak AD-RH 5 µm 150*4.6 mm from Daicel®
Eluent: –A: Water with 0.1% by volume $H_3PO_4$
–B: Acetonitrile with 0.1% by volume $H_3PO_4$

| Time in min | % B | Flow |
|---|---|---|
| 0.0 | 30 | 1.2 |
| 25.0 | 70 | 1.2 |
| 30.0 | 100 | 1.2 |
| 40.0 | 100 | 1.2 |
| 40.1 | 30 | 1.2 |

Detector: UV-Detector λ=205 nm, BW=5 nm
Flow rate: 1.2 ml/min
Injection: 5 µL
Temperature: 40° C.
Run time: 45 min
Pressure: ca. 70 bar B) Preparation Examples Example 1: WITTIG Reaction Starting from the Cyclopropylphosphonium Salt with Potassium Tert-Butylate

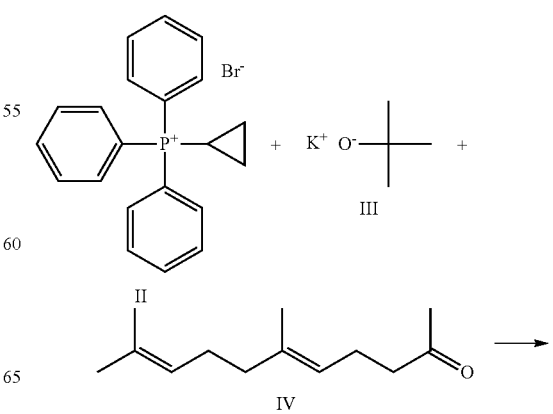

-continued

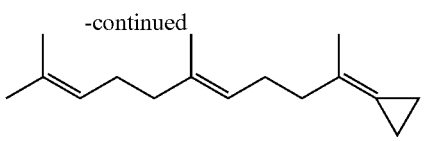

Feed Materials:

| 640 ml<br>598.96 g | (7890.58 mmol) | I | Tetrahydrofuran<br>M = 72.11 g/mol | 24.7 eq |
| --- | --- | --- | --- | --- |
| 122.6 g | (320 mmol) | II | Cyclopropyl-<br>phosphonium salt<br>M = 383.27 g/mol | 1 eq |
| 35.91 g | (320 mmol) | III | Potassium tert-butylate<br>M = 112.21 g/mol | 1 eq |
| 48.6 g | (288 mmol) | IV | E-Geranyl acetone<br>M = 194.32 g/mol | 0.9 eq |

The reactor is flushed with nitrogen. 500 ml of THF (I) are introduced as initial charge and cooled to 0° C. Cyclopropylphosphonium salt (II) comminuted in the mortar is added rinsed with the remaining amount (140 ml) of THF (I) and stirred at 0° C. for 8 min. Under an $N_2$ atmosphere, potassium tert-butylate (III) is added, during which the internal temperature increases to 5° C. The suspension becomes immediately red-orange, and is then stirred at ca. 0° C. for 2 hours.

Geranyl acetone (IV) is added dropwise over the course of ca. 10 min (slight exothermyl), then stirring is carried out for 15 min at an oil temperature of −2° C. The reaction mixture is then heated with delta 1° C. (oil temperature to internal temperature). When an internal temperature of 35° C. is reached, stirring is continued overnight at an oil temperature of 35° C. After a total stirring time of 24 h (conversion check via TLC: n-heptane/EE=10:1), the mixture is worked up. At an internal temperature of 35° C., 1000 ml of n-heptane are added to the reaction suspension, and distillate is drawn off by regulating the vacuum such that the internal temperature does not exceed 35° C.; heating with delta 15° C. relative to the internal temperature. At a pressure of 155 mbar, the oil temperature is reduced to 35° C., then aerated with $N_2$. Distillate and cold trap are emptied. (Fraction 1: 494 g, of which 259 g THF according to GC A %). The apparatus is evacuated to 150 mbar. By regulating the vacuum, distillate is drawn off such that the internal temperature does not exceed 35° C.; heating with delta 15° C. relative to the internal temperature. At a pressure of 95 mbar, the oil temperature is reduced to 20° C., then aerated with $N_2$. Distillate and cold trap are emptied (fraction 2: 292 g, of which 63 g THF according to GC A %). In total, ca. 320 g of THF (according to GC A %, although n-heptane is over evaluated) of 569 g was distilled off.

530 g of water are stirred into the reactor contents (suspension, 20° C.), phase separation after ca. 5 min. The lower phase 1 (LP1, 395 g, pale brown) is discarded. The upper phase 1 with TPPO detritus is stirred with 500 ml of water for 5 min, phase separation after 5 min. The lower phase 2 (LP2, 559 g, pale brown) is discarded. The upper phase 2 with TPPO detritus is stirred with 500 ml water/methanol (1:1 parts by volume, 455 g) for 5 min; the stirrer is switched off. The TPPO is not completely dissolved in the water/MeOH. Phase separation takes place after 5 min, Lower phase 3 (LP3, 545 g, cloudy phase). The upper phase 3 with TPPO detritus is stirred with 500 ml of water/methanol (1:1 parts by volume, 455 g) for 5 min; the stirrer is switched off. The TPPO is now completely dissolved, clear phases! Phase separation takes place after 5 min. Lower phase 4 (LP4, 557 g, cloudy phase). The upper phase 4 is stirred again with 500 ml of water/methanol (1:1 parts by volume, 455 g) for 5 min; the stirrer is switched off. Virtually clear phases are observed! Phase separation takes place after 5 min. Lower phase 5 (LP5, 454 g, slightly cloudy phase). The upper phase 5 is washed again with 500 ml of water, the phases are separated. Lower phase 6 (LP6, 509 g, clear phase) is discarded. The upper phase 6 (303 g) is concentrated on a rotary evaporator (45° C. bath, full oil-pump vacuum).

This gives 60.4 g of product of value (yellow oil). The desired product was able to be isolated with ca. 97.2 A % purity (E&Z) and about 93% yield, based on geranyl acetone; based on C3-phosphonium salt, the yield is 84.0%.

HPLC Method 2

| RT | Substance | Area % |
| --- | --- | --- |
| 6.14 | TPPO | 1.51 |
| 10.79 | E-Geranyl acetone | 0.24 |
| 20.64 | Z-C16-cyclopropane | 6.03 |
| 22.25 | E-C16-cyclopropane | 91.21 |

Example 2: Wittig Reaction Starting from the TPP-Bromopropane Salt with NaH

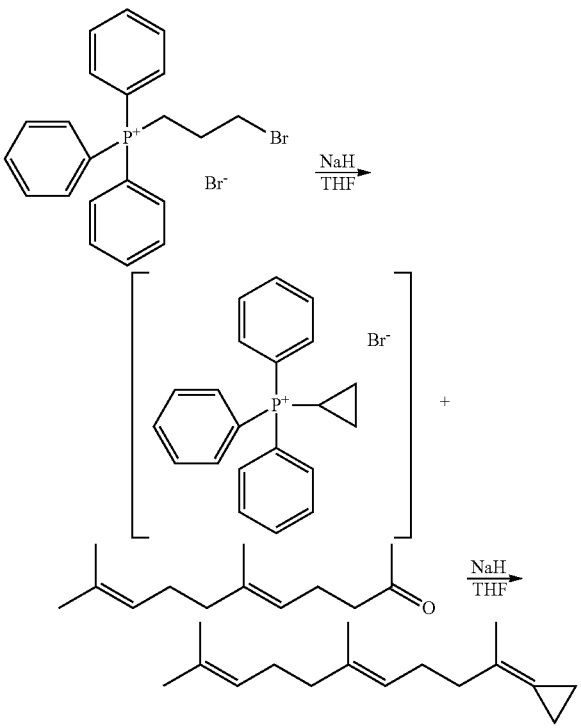

Feed Materials:

| 250 ml<br>222.25 g | (3082.3 mmol) | I | Tetrahydrofuran<br>M = 72.11 g/mol | 12.3 eq |
| --- | --- | --- | --- | --- |
| 126.6 g | (250 mmol) | II | $C_4$ salt HPLC - 91.67%<br>by weight | 1 eq |

| | | | | | |
|---|---|---|---|---|---|
| 22 g | (550 mmol) | III | Sodium hydride in mineral oil 60% strength M = 24 g/mol | 2.2 eq | |
| 48.6 g | 240.1 mmol based on (E) and (Z) 225 mmol based on (E) | IV | Geranyl acetone 90%(E) and 6%(Z) M = 194.32 g/mol | 0.96 eq 0.9 eq | |

The $C_4$ salt (II) is introduced as initial charge at room temperature in THF (I). The sodium hydride (III) is washed 3× with in each case 100 ml of n-hexane, dried in the nitrogen stream and added. The white suspension is then stirred for 4.5 h at room temperature (conversion check via HPLC). Geranyl acetone (IV) is then added and the mixture is heated at 35° C. for 21 h. 500 ml of n-heptane are then added to the yellowish suspension. THF is then removed on a rotary evaporator. The remaining suspension is admixed with 500 ml of water/methanol and the phases are separated. The aqueous phase is extracted 2× with 250 l of n-heptane. The combined organic phases are washed 6× with 250 ml water/methanol in order to separate off formed NaBr and TPPO. The organic phase is dried over sodium sulfate and concentrated on a rotary evaporator at 50° C./10 mbar. This gives 50.6 g of product of value in the form of a brown, clear oil.

| Geranyl acetone | 100% Yield | Yield (%) based on Σ E&Z area % | | Yield (%) based on Σ E&Z area % | | Yield (%) based on E-$C_{16}$-cyclopropane area % | |
|---|---|---|---|---|---|---|---|
| [mmol] | [g] | [g] | [%] | [g] | [%] | [g] | [%] |
| 240 | 52.4 | 49.3 | 94.2 | 49.2 | 93.9 | | |
| 225 | 49.1 | | | | | 46.1 | 94.0 |

HPLC Method 2:

| Sample: RT | 36257/ Substance | A Area % |
|---|---|---|
| 2.68 | $C_3$ salt | |
| 3.27 | $C_4$ salt | |
| 6.05 | TPPO | |
| 10.65 | E-Geranyl acetone | 0.4 |
| 20.57 | Z-$C_{16}$-cyclopropane | 6.0 |
| 22.16 | E-$C_{16}$-cyclopropane | 91.2 |

HPLC Method 1:

| | | A | |
|---|---|---|---|
| Sample: RT | 36257/ Substance | Area % | % by weight |
| 1.05 | $C_3$ salt | | |
| 1.10 | $C_4$ salt | | |
| 1.27 | TPPO | | |
| 3.64 | Geranyl acetone | | |
| 14.53 | $C_{16}$-cyclopropane | 97.2 | 97.5 |

Example 3: Ring Opening with $BF_3$ Etherate and Glacial Acetic Acid

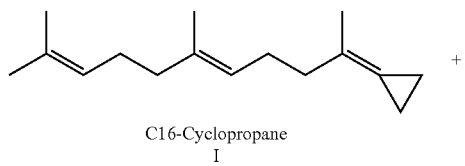

C16-Cyclopropane
I

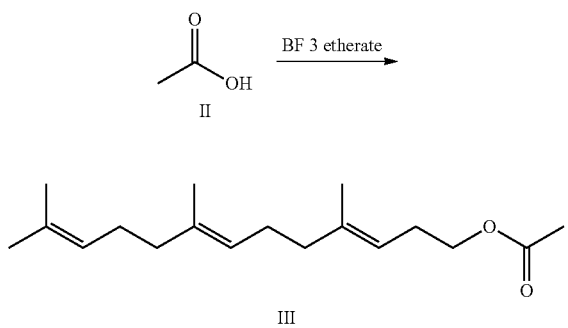

Feed Materials:

| Substance | Purity % | Molecular Weight g/mol | Mass g | Quantitative Amount Mol | Eq |
|---|---|---|---|---|---|
| $C_{16}$-cyclopropane | 90.3 (based on E & Z) | 218.38 | 109.2 | 0.452 | 1 |
| Glacial acetic acid | 100 | 60.05 | 1914 | 31.875 | 70.5 |
| $BF_3$ etherate | 100 | 141.93 | 9.05 | 0.0638 | 0.14 |
| Glacial acetic acid | 100 | 60.05 | 204 | 3.4 | 7.5 |

The $C_{16}$-cyclopropane (I) is dissolved in glacial acetic acid (II) and produces a clear, yellow solution. The $BF_3$ etherate is prediluted in glacial acetic acid and added over the course of 2 min at RT. The solution slowly becomes darker, no heat tonality. Stirring is carried out overnight at RT. A dark brown, clear solution (HPLC analysis) is obtained. After 27 h at RT, 2.5 l of water and 1 l of cyclohexane are added to the clear, dark brown solution, and the phases are separated. The aqueous phase is extracted twice with 0.5 l cyclohexane. The combined organic phases are washed in succession with 4×0.2 l of water, 0.25 l of saturated $NaHCO_3$ solution and again 0.25 l of water. The organic upper phase is dried over sodium sulfate and concentrated on a rotary evaporator at 40° C./4 mbar. This gives 122.5 g of product of value in the form of an orange liquid crude product (theory 118.3 g) (HPLC analysis method 2: A). The homofarnesyl acetate is obtained in a 3Z,7E: 3E,7E ratio of 1:2.45.

In the case of the first aqueous phase, a further ca. 150 ml of organic phase separated out overnight. This was isolated and likewise washed several times with water and saturated NaHCO$_3$. The organic upper phase was dried over sodium sulfate and concentrated on a rotary evaporator at 40° C./4 mbar. This gives a further 7.0 g of product of value (HPLC analysis method 2: B).

| HPLC Method 2: Area % | | | | | | | | | |
|---|---|---|---|---|---|---|---|---|---|
| | | | min | | | | | | |
| | 10.70 Geranyl acetone | 14.10 12-Acetoxy- Hofa acetate stereoisomers | 15.18 | 16.61 17.78 3E/Z,7Z-Hofa acetate | | 18.84 3Z,7E- Hofa acetate | 20.13 3E,7E- Hofa acetate | 20.68 Z-C16- cyclo- propane | 22.27 E-C16- Cyclo- propane | >28 |
| Starting material | 5.1 | 0 | 0 | 0 | 0 | 0 | 0 | 5.7 | 84.6 | 0.1 |
| A | 3.6 | 3.4 | 7.1 | 2.8 | 6.8 | 17.2 | 42.1 | 0 | 0.2 | 7.9 |
| B | 3.6 | 2.6 | 6.6 | 2.1 | 6.9 | 16.1 | 40.5 | 0 | 0.3 | 8.3 |

The desired product was able to be isolated with ca. 60% purity and about 62% yield. A post-extraction of the first aqueous phase was able to increase the yield to 65%.

Example 4: Ring Opening with AlCl$_3$ and Glacial Acetic Acid

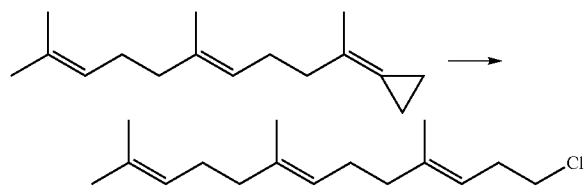

Feed Materials:

| Substance | Purity % | Molecular Weight g/mol | Mass g | Quantitative amount mol | Eq |
|---|---|---|---|---|---|
| C$_{16}$-cyclopropane | 94.6 (based on E & Z) 88.7 (based on E) | 218.38 | 34.5 | 0.15 | 1 |
| Glacial acetic acid | 100 | 60.05 | 192.4 | 3.2 | 21 |
| Aluminum trichloride | 100 | 133.34 | 7.27 | 0.055 | 0.36 |

The C$_{16}$-cyclopropane is introduced as initial charge in glacial acetic acid at room temperature. Aluminum trichloride is added. Stirring is carried out for 17.5 h at room temperature (conversion check via thin-layer chromatography and HPLC). The reaction mixture is then admixed with 600 ml of water and extracted 2× with 200 ml of cyclohexane. The organic phases are combined (pH=3-4) and washed with 120 g of NaOH (5% strength). The organic phase is dried over sodium sulfate and concentrated on a rotary evaporator at 50° C./10 mbar. This gives 35.4 g of product of value in the form of an orange liquid, i.e. at a purity of 96.4 HPLC area % in a yield of 90% based on the sum of the isomers.

HPLC Method 2:

| Sample: RT | Substance | A Area % | Ratio E/Z |
|---|---|---|---|
| 10.65 | E-Geranyl acetone | 0.4 | |
| 20.35 | 3Z,7Z-homofarnesyl chloride | 1.8 | 1 |
| 20.69 | C$_{16}$-cyclopropane Z | | |
| 21.29 | 3Z,7E-homofarnesyl chloride | 4.4 | 2.4 |
| 22.27 | C$_{16}$-cyclopropane E (identical to 3E,7Z-homofarnesyl chloride) | | |
| 22.27 | 3E,7Z-homofarnesyl chloride | 24.1 | 1 |
| 23.79 | 3E,7E-homofarnesyl chloride | 66.1 | 2.7 |

Σ 96.4 Area %

Example 5: Substitution of the Homofarnesyl Chloride to Give Homofarnesol

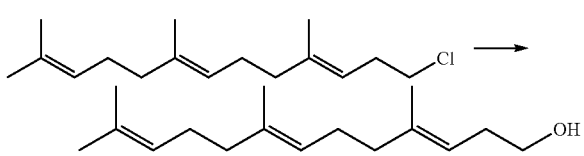

Feed Materials:

| Substance | Purity [%] | Molecular weight [g/mol] | Mass/ volume | Quantitative amount [mol] | Eq |
|---|---|---|---|---|---|
| Homofarnesyl chloride | 96.3 (based on all homofarnesyl chloride isomers) | 254.842 | 12.6 g | 0.0475 | 1 |

| Substance | Purity [%] | Molecular weight [g/mol] | Mass/ volume | Quantitative amount [mol] | Eq |
|---|---|---|---|---|---|
| | 1:2.7 3E,7Z:3E,7E 1:2.4 3Z,7Z:3Z,7E | | | | |
| Toluene | | | 10 mL | | |
| Sodium formate | 97 | 68.01 | 19.4 g | 0.285 | 6 |
| Tetrabutyl- ammonium bromide | | 322.38 | 2.28 g | 0.0071 | 0.15 |
| NaOH | 25 | 40 | 7.6 g | 0.0475 | 1 |

Homofarnesyl chloride is introduced as initial charge in toluene at room temperature. Sodium formate and tetrabutylammonium bromide are added. The suspension is brought to 110° C. and stirred for 10 h (conversion check via HPLC; sample preparation: 1 ml of reaction mixture is stirred with 1 ml of NaOH 25% strength for 1 h at room temperature. Toluene phase→HPLC). The reaction mixture is then admixed with 25% strength NaOH and stirred for 60 min at room temperature (ph=10-11). The present suspension is then added to 300 ml of dist. water and extracted with 100 ml of toluene. The organic phase is washed 1× with 150 ml, 1× with 100 ml demineralized water, dried over sodium sulfate and evaporated to dryness on a rotary evaporator at 50° C./10 mbar. This gives 11.1 g of product of value in the form of a brown, clear oil, i.e. at a purity of 71.4 HPLC area % in a yield of 70%, based on the sum of the isomers 3E,7E- and 3E,7Z-homofarnesol.

HPLC Method 2:

| Sample: RT | Substance | Area % | Ratio E/Z |
|---|---|---|---|
| 13.59 | 3E,7Z-homofarnesol | 17.6 | 1 |
| 14.79 | 3E,7E-homofarnesol | 53.8 | 3.1 |

Example 6: Chemical Cyclization of Homofarnesol to Give Ambrox

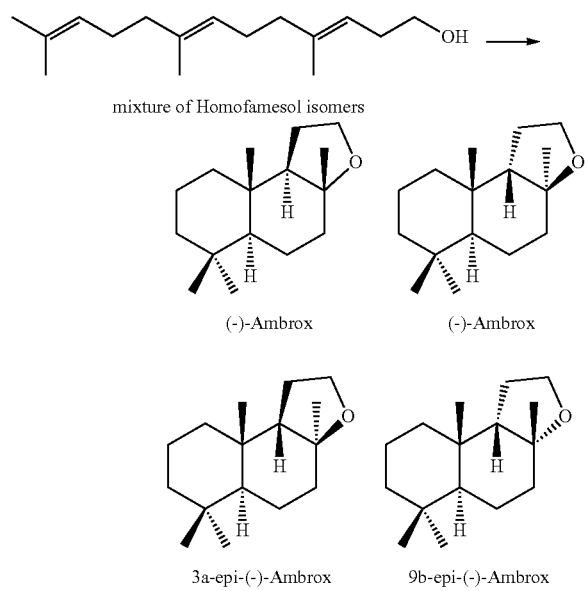

Various process variants for a chemical cyclization are described below:
a) Conditions: 2-nitropropane, conc. sulfuric acid, −78° C.
Feed Materials:

| Substance | Purity % | Molecular weight g/mol | Mass/ volume | Quantitative amount mol | Eq |
|---|---|---|---|---|---|
| Homofarnesol | 90.1 (3Z,7E: 5% and 3E,7E: 85.1% chiral HPLC) | 236.4 | 1 g | 0.00423 | 1 |
| Conc. sulfuric acid | | 98.08 | 3.9 g/ 2.12 mL | 0.04 | 9.4 |
| 2-Nitropropane | | 89.09 | 99.2 g/ 100 mL | | |

Conc. sulfuric acid was introduced as initial charge in 50 ml of 2-nitropropane under a nitrogen atmosphere at −78° C. A solution of 1 g of homofarnesol in 50 ml of 2-nitropropane was added dropwise at −78° C. over the course of 30 min. Reaction control was carried out via TLC: after 2 h, the starting material was used up. For the work-up, the reaction mixture was brought to 0° C. and then slowly added to 200 ml of saturated NaHCO$_3$ solution. Extraction was carried out three times with 100 ml of diethyl ether. The organic phases were combined and washed with 100 ml of saturated sodium chloride solution, dried over sodium sulfate and evaporated to dryness on a rotary evaporator. An isomer mixture of at least (−) and (+)-ambrox and 9b-epi-(−)-ambrox and 3a-epi (+)-ambrox (see above) was obtained.
b) Conditions: 2-nitropropane, trifluoromethanesulfonic acid, −78° C.
Feed Materials:

| Substance | Purity % | Molecular weight g/mol | Mass/ volume | Quantitative amount mol | Eq |
|---|---|---|---|---|---|
| Homofarnesol | 90.1 (3Z,7E: 5% and 3E,7E: 85.1% chiral HPLC) | 236.4 | 1 g | 0.00423 | 1 |
| Trifluoromethane- sulfonic acid | | 150.08 | 6 g/ 3.54 ml | 0.04 | 9.4 |
| 2-Nitropropane | | 89.09 | 99.2 g/ 100 ml | | |

Trifluoromethanesulfonic acid was introduced as initial charge in 50 ml of 2-nitropropane under a nitrogen atmosphere at −78° C. A solution of 1 g of homofarnesol in 50 ml of 2-nitropropane was added dropwise at −78° C. over the course of 30 min. The reaction control was carried out via TLC: after 2 h, the starting material was used up. For the work-up, the reaction mixture was brought to 0° C. and then slowly added to 200 ml of saturated NaHCO$_3$ solution. Extraction was carried out 3 times with 100 ml of diethyl ether. The organic phases were combined and washed with 100 ml of saturated sodium chloride solution, dried over sodium sulfate and evaporated to dryness on a rotary evaporator. An isomer mixture of at least (−) and (+)-ambrox and 9b-epi-(−)-ambrox and 3a-epi+)-ambrox (see above) was obtained.

c) Conditions: 2-nitropropane, fluorosuifonic acid, −78° C.

(see P. F. Vlad et al. *Khimiya Geterotsiklicheskikh Soedinenii, Engl. Transl.* 1991, 746)

Feed Materials:

| Substance | Purity % | Molecular weight g/mol | Mass/ volume | Quantitative amount mol | Eq |
|---|---|---|---|---|---|
| Homofarnesol | 83.3 (3Z,7E: 3E,7E = 1:15,1) | 236.4 | 1 g | 0.00423 | 1 |
| Fluorosulfonic acid | | 100.07 | 4 g | 0.04 | 9.4 |
| 2-Nitropropane | | 89.09 | 99.2 g/ 100 ml | | |

Fluorosulfonic acid was introduced as initial charge in 50 ml of 2-nitropropane under a nitrogen atmosphere at −90° C. A solution of 1 g of homofarnesol in 50 ml of 2-nitropropane was added dropwise at −90° C. Stirring was carried out for a further 25 h at 78° C. For the work-up, the reaction mixture was brought to 0-5° C. and then slowly added to 200 ml of saturated NaHCO$_3$ solution. Extraction was carried out 3 times with 100 ml of diethyl ether. The organic phases were combined and washed with 100 ml of saturated sodium chloride solution, dried over sodium sulfate and evaporated to dryness on a rotary evaporator. An isomer mixture of at least (−) and (+)-ambrox and 9b-epi-(−)-ambrox and 3a-epi-(−)-ambrox (see above) was obtained and separated via kugelrohr distillation.

Reference is made expressly to the disclosure of the documents mentioned herein.

The invention claimed is:

1. A process for preparing compounds of formula I

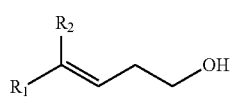
(I)

in which

R$_1$ is a straight-chain or branched, optionally mono- or polyunsaturated hydrocarbyl radical, and R$_2$ is H or C$_1$-C$_6$-alkyl, where a) a carbonyl compound of formula II

(II)

in which R$_1$ and R$_2$ have the meanings above, is reacted by means of Wittig olefination to give a cyclopropane of formula (III)

(III)

b) the cyclopropane of the formula III is reacted, with ring opening, to give a compound of formula IV

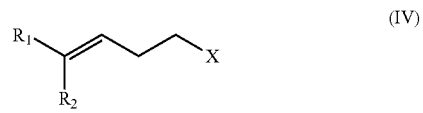
(IV)

in which X is halogen or O—R', in which R' is H, acyl, Tf-acetyl or SO$_2$—R", and R" is alkyl or aryl; and c) the compound of the formula IV is converted to the formula I compound.

2. The process according to claim 1, where a cyclopropylphosphonium salt is used for the Wittig olefination according to stage a).

3. The process according to claim 2, in which the cyclopropylphosphonium salt is a triphenylphosphonium compound of formula V

(V)

in which Z$^−$ is the anion of a strong acid.

4. The process according to claim 3, where the compound of the formula V is prepared by reacting a) bromobutyrolactone with triphenylphosphine and thermally decarboxylating the reaction product, or by reacting b) 1,3-dibromopropane with triphenylphosphine and cyclizing the reaction product.

5. The process according to claim 1, wherein the ring-opening in stage b) takes place in the presence of a Lewis acid or Brönstedt acid/protonic acid, and a nucleophile.

6. The process according to claim 5, where the ring opening of step b) provides E-selectively with respect to R$_1$, where E:Z is greater than 1.5.

7. The process according to claim 1, wherein for stage c), X is OR', and carrying out an ester cleavage, or X is halogen, and converting the halide to a corresponding ester, and then cleaving the corresponding ester.

8. The process according to claim 1, wherein the formula I compound is (3E,7E)-homofarnesol of formula Ia (Ia)

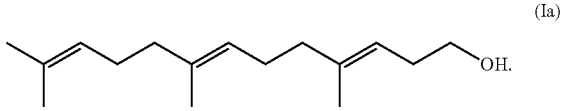 [SMILES: CC(C)=CCC/C(C)=C/CC/C(C)=C/CCO]

9. The process according to claim 8, where, in stage a), E-geranyl acetone of formula IIa (IIa)

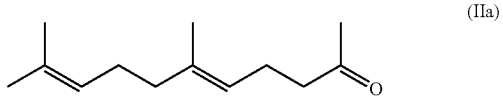

is reacted with cyclopropylphosphonium halogenide to provide a compound of formula IIIa (IIIa)

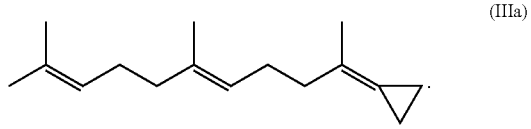 [SMILES: CC(C)=CCC/C(C)=C/CCC(C)=C1CC1]

10. A process for preparing enantiomerically pure ambrox or a stereoisomer mixture of ambrox, where (3E,7E)-homofarnesol is prepared by a process according to claim 1 and the (3E,7E)-homofarnesol is cyclized to give enantiomerically pure (−)-ambrox, 3aR,5aS,9aS,9bR)-3a,6,6,9a-tetramethyldodecahydronaphtho[2,1-b]furan, or a stereoisomer mixture of 3aR,5aS,9aS,9bR)-3a,6,6,9a-tetramethyldodecahydronaphtho[2,1-b]furan.

11. The process according to claim 6, where the E-selectivity with respect to $R_1$ is a molar excess of E:Z in a range from 2:1 to 50:1.

12. The process according to claim 1, where $R_1$ is a $C_1$-$C_{20}$ hydrocarbyl radical with one or more conjugated or non-conjugated double bond.

13. The process according to claim 12, where $R_2$ is a methyl or ethyl.

14. The process according to claim 1, where $R_2$ is a methyl or ethyl.

15. The process according to claim 14, where $R_1$ is a $C_1$-$C_{20}$ hydrocarbyl radical with one or more non-conjugated radicals of formula

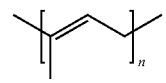

where n is 2, 3, or 4.

* * * * *